(12) United States Patent
Mikulas et al.

(10) Patent No.: US 7,154,006 B2
(45) Date of Patent: Dec. 26, 2006

(54) PREPARATION OF FLUORINATED ANILINES

(75) Inventors: Mark Mikulas, Leverkusen (DE); Albrecht Marhold, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 195 days.

(21) Appl. No.: 10/965,301

(22) Filed: Oct. 14, 2004

(65) Prior Publication Data

US 2005/0101795 A1    May 12, 2005

(30) Foreign Application Priority Data

Oct. 15, 2003    (DE)    ............... 103 47 932

(51) Int. Cl.
*C07C 209/52*    (2006.01)
*C07C 245/08*    (2006.01)

(52) U.S. Cl. ............... 564/415; 564/412; 534/558

(58) Field of Classification Search ............... None
See application file for complete search history.

(56) References Cited

U.S. PATENT DOCUMENTS

| 6,184,425 B1 | 2/2001 | Kolomeitsev et al. | ...... 570/170 |
| 6,284,762 B1 | 9/2001 | Pfrengle | ............ 514/258 |
| 2003/0036667 A1 | 2/2003 | Henrich et al. | ............ 570/145 |

FOREIGN PATENT DOCUMENTS

WO        98/46607        10/1998

OTHER PUBLICATIONS

Database CAPLUS on STN, Acc. No. 1976:17276, Sindelar et al., Collections of Czechoslovak Chemical Communications (1975), 40(6), p. 1940-1959 (abstact).*

Database CAPLUS on STN, Acc. No. 1978:22255, Banks et al., Journal of the Chemical Society, Perkin Transactions 1: Organic and Bio-Organic Chemistry (1972-1999) (1977), 15, p. 1746-1749 (abstract).*
J. Org. Chem., 1962, vol. 27, pp. 1910-1911; W. G. Dauben et al "Photochemical Transformations. XI. Isomerization of 1,3-Cyclooctadience".
J. Fluor. Chem., 2002, 113, (2), pp. 207-209; Min Shi et al, "Perfluorinated Rare Earth Metals Catalyzed Nitration of Aromatic Compounds".
Tetrahedron, 1999, 55, pp. 7725-7738; D. J. Adams et al, "The Effect of Basicity on Fluorodenitration Reactions Using Tetramethylammonium Salts".
J. Am. Chem. Soc., 1956, vol. 78, pp. 6034-6037; G. C. Finger et al, "Aromatic Fluorine Compounds. VII> Replacement of Aromatic -Cl and -NO$_2$ Groups by -F$^{1,2}$".
Tetrahedron, 2002, 43, 7, pp. 1329-1331; S. Gowda et al, "Reductive Cleavage of Azo Compounds Catalyzed by Commercial Zinc Dust Using Ammonium Format or Formic Acid".
Database Beilstein, Beilstein Institut zur Förderung der Chemischen Wissenschaft, Frankfurt am Main, De; XP002318170, Gefunden im Xfire, Database Accession No. 980172, 3770516 *Zusammenfassung* & Farmaco Ed. Sci., Bd. 39, Nr. 5, 1984, Seiten 403-413.
Database Beilstein, Beilstein Institut zur Förderung der Chemischen Wissenschaft, Frankfurt am Main, DE; XP00231871, Gefunden Im Xfire, Database Accession No. 3631130, 3751924 *Zusammenfassung* & J. Med. Chem., Bd. 33, Nr. 7, 1990, Seiten 2019-2024.
Erich Baer and Anthony L. Tosoni: Formation of Symmetric Azocompounds from Primary Aromatic Amines by Lead Tetraacetate:, J. Am. Chem. Soc., Bd. 78, 1956, Seiten 2857-2858, XP002318169 *das ganze Dokument*.
Database Beilstein, Beilstein Institut zur Förderung der Chemischen Wissenschaft, Frankfurt am Main, DE; XP002318172, Gefunden Im Xfire, Database Accession No. 4062896 *Zusammenfassung* & J. Chem. Soc., 1965, Seiten 2621-2627.

* cited by examiner

*Primary Examiner*—Brian Davis
(74) *Attorney, Agent, or Firm*—Michael A. Miller

(57) ABSTRACT

The invention relates to a process for preparing fluorinated anilines starting from the corresponding chlorinated anilines, and also to the use of the fluorinated anilines.

9 Claims, No Drawings

PREPARATION OF FLUORINATED ANILINES

The invention relates to a process for preparing fluorinated anilines starting from the corresponding chlorinated anilines, and also to the use of the fluorinated anilines.

Fluorinated anilines are important intermediates for preparing active pharmaceutical ingredients and agrochemicals, as specified, for example, in WO-A 98/46607 and WO 98/46608.

Known processes for their preparation include, for example, the nitration of fluorinated aromatics and the subsequent reduction of the nitro compounds to the corresponding anilines. In this process, for example, 4-fluoroaniline and 2,4-difluoroaniline can be obtained from fluorobenzene and 1,3-difluorobenzene respectively (see J. Org. Chem., 1962, 27, 1910–11; J. Fluor. Chem., 2002, 113 (2), 207–9). A disadvantage of this method is that the fluorinated aromatics are very expensive and the nitration only allows a restricted substitution pattern on the aromatic ring.

A further process for preparing fluorinated anilines is the Hofmann degradation of fluorinated benzamides. In this process, 2,6-difluoroaniline can be prepared, which is not accessible by the above-described route. However, the yields for this degradation are only moderate, which is why this method cannot be considered for industrial application.

A further process for preparing fluorinated anilines proceeds starting from chloronitrobenzenes via a chlorine-fluorine exchange reaction (halex reaction) with subsequent hydrogenation directly to the desired products. The nitro group activates chlorine atoms in the 2-, 4- and 6-position, so that it is possible in this way to obtain, for example, 2,4-difluoroaniline from 2,4-dichloronitrobenzene after halex reaction and reduction (see Tetrahedron, 1995, 51, 6363). However, in the case of more highly chlorinated nitrobenzenes or in the presence of substituents which activate the nitro group for the halex reaction, this method generally fails (see Tetrahedron, 1999, 55, 7725–7738; J. Am. Chem. Soc. 1956, 78, 6034).

There is therefore still a need for a process for preparing fluorinated anilines which overcomes the above-described disadvantages and enables simple access to fluorinated anilines.

A process has now been found for preparing compounds of the formula (I)

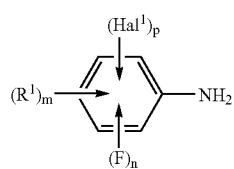

in which m is an integer in the range from 0 to (5-n-p)

n is 1, 2, 3 or 4 and p is 0, 1 or 2, where the sum of n+p is a maximum of 4 and $R^1$ is in each case independently hydrogen, fluorine, $C_1$–$C_{12}$-alkyl, $C_5$–$C_{14}$-aryl, $C_6$–$C_{15}$-arylalkyl, $C_1$–$C_{12}$-fluoroalkyl, $C_1$–$C_{12}$-fluoroalkylthio, $C_1$–$C_{12}$-fluoroalkoxy, $C_1$–$C_{12}$-alkylsulphonyl or radicals of the formulae (IIa) to (IIf)

A-CN  (IIa)

A-CON($R^2$)$_2$—  (IIb)

A-CO$_2R^2$  (IIc)

A-CONH$_2$  (IId)

A-COHal$^2$  (IIe)

A-B—$R^2$  (IIf)

where, in the formulae (IIa) to (IIf),

A is absent or is a $C_1$–$C_8$-alkylene or $C_1$–$C_8$-fluoroalkylene radical and B is oxygen or $NR^2$, and $R^2$ is in each case independently $C_1$–$C_8$-alkyl, $C_6$–$C_{15}$-arylalkyl or $C_5$–$C_{14}$-aryl, or $N(R^2)_2$ as a whole is optionally a cyclic amino radical having a total of 4 to 12 carbon atoms and Hal$^1$ is chlorine or bromine, which is characterized in that, in a step A), compounds of the formula (III)

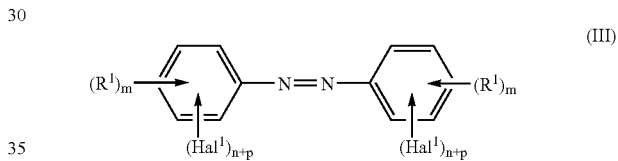

in which $R^1$, Hal$^1$, m, p and n are each as defined above are converted in the presence of ionic fluoride to compounds of the formula (IV)

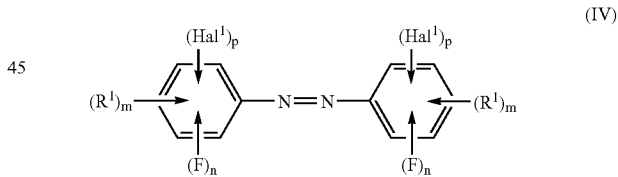

and, in a step B), the compounds of the formula (IV) are converted to compounds of the formula (I) with a reducing agent.

In the context of the invention, all radical definitions, parameters and illustrations above and listed hereinbelow, in general or within areas of preference, i.e. the particular areas and areas of preference, may be combined as desired.

Alkyl and alkylene are in each case independently a straight-chain, cyclic, branched or unbranched alkyl and alkylene radical respectively. The same applies to the non-aromatic moiety of an arylalkyl radical. Specific but non-limiting examples thereof are:

$C_1$–$C_4$-Alkyl is, for example, methyl, ethyl, n-propyl, isopropyl, n-butyl, sec-butyl and tert-butyl, and $C_1$–$C_{12}$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, n-heptyl, n-octyl, n-nonyl, n-decyl and n-dodecyl.

$C_1$–$C_8$-Alkylene which is, for example, methylene, 1,1-ethylene, 1,2-ethylene, 1,1-propylene, 1,3-propylene, 1,4-butylene, 1,2-cyclohexoxylene and 1,2-cyclopentylene.

$C_2$–$C_8$-Alkenyleneis which is, for example, 1,1-ethenylene, 2-ethoxy-1,1-ethenylene and 2-methoxy-1,1-ethenylene.

Fluoroalkyl and fluoroalkylene are in each case independently a straight-chain, cyclic or a branched or unbranched alkyl radical and alkylene radical respectively, each of which is singly, multiply or fully substituted by fluorine atoms.

For example, $C_1$–$C_{12}$-fluoroalkyl is trihluoromethyl, 2,2,2-trifluoroethyl, pentafluoroethyl, nonafluorobutyl, heptafluoroisopropyl, perfluorooctyl and perfluorododecyl. Specific but non-limiting examples thereof are:

Aryl is in each case independently an aromatic radical having 5 to 14 skeleton carbon atoms of which no, one, two or three skeleton carbon atoms per cycle, but at least one skeleton carbon atom in the entire molecule, may be substituted by heteroatoms selected from the group of nitrogen, sulphur and oxygen, or preferably a carbocyclic aromatic radical having 6 to 14 skeleton carbon atoms.

In addition, the carbocyclic aromatic radical or heteroaromatic radical may be substituted by up to five identical or different substituents per cycle which are selected from the group of fluorine, cyano, nitro, $C_1$–$C_{12}$-alkyl, $C_1$–$C_{12}$-fluoroalkyl, $C_1$–$C_{12}$-fluoroalkoxy, $C_1$–$C_{12}$-fluoroalkylthio, $C_1$–$C_{12}$-alkoxy, di($C_1$–$C_8$-alkyl)amino or radicals of the formulae (IIa) to (IIf) as defined above.

Arylalkyl is in each case independently a straight-chain, cyclic, branched or unbranched alkyl radical as defined above which may be singly, multiply or fully substituted by aryl radicals as defined above.

The preferred substitution patterns are defined hereinbelow:

n is preferably 1, 2 or 3, more preferably 3, $R^1$ is preferably hydrogen, $C_1$–$C_4$-alkyl, trifluoromethyl, halocarbonyl, or cyano, more preferably hydrogen.

In compounds of the formula (I), p is preferably 0.

The process according to the invention is especially suitable for preparing 2,4,6-trifluoroaniline, 2-trifluoromethyl4-fluoroaniline, 4-trifluoromethyl-2-fluoroaniline, 4-trifluoromethyl-2,6-difluoroaniline and 3-trifluoromethyl-2,4,6-trifluoroaniline.

The compounds of the formula (III) which are used as reactants are preferably prepared in such a way that, in a first step, compounds of the formula (V) are halogenated, preferably chlorinated, to give compounds of the formula (VI), where, in the formulae (V) and (VI)

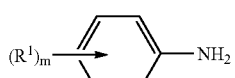

(V)

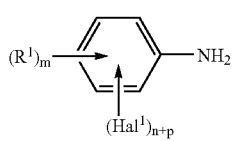

(VI)

$R^1$, $Hal^1$, n, p and m are each as defined above and, in a second step, the compounds of the formula (VI) are oxidized to the compounds of the formula (III).

Preferred compounds of the formula (VI) are 2,4,6-trichloroaniline, 2-trifluoromethyl-4-chloroaniline, 4-trifluoromethyl-2-chloroaniline, 4-trifluoromethyl-2,6-dichloroaniline and 3-trifluoromethyl-2,4,6-trichloroaniline.

Some compounds of the formula (III) are hitherto unknown, but are accessible by the above-described process. The invention therefore also encompasses 2,2'-dichloro-4,4'-bistrifluoro-methylazobenzene, 2,2',6,6'-tetrachloro-4,4'-bistrifluoromethylazobenzene, 2,2',4,4',6,6'-hexachloro-3,3'-bistrifluoromethylazobenzene and 4,4'-dichloro-2,2'-bistrifluoromethyl-azobenzene.

Some compounds of the formula (IV) which are indispensable intermediates for the process according to the invention are likewise hitherto unknown. The invention therefore also encompasses 2,2'-difluoro4,4'-bistrifluoromethylazobenzene, 2,2',6,6'-tetrafluoro-4,4'-bistri-fluoromethylazobenzene, 2,2',4,4',6,6'-hexafluoro-3,3'-bistrifluoromethylazobenzene and 4,4'-difluoro-2,2'-bistrifluoromethylazobenzene.

Both the halogenation of anilines and the oxidation of anilines or their salts to the corresponding diazobenzenes are known in principle, for example, from Bull. Soc. Chim. Belg., 1993, 102 (1), 59–62; Org. Synth., 1960, 40, 18) and can be applied to the compounds of the formulae (V) and (VI).

In step A) of the process according to the invention, compounds of the formula (III) are converted to compounds of the formula (IV) in the presence of ionic fluoride.

Ionic fluorides are, for example, quaternary ammonium fluorides or phosphonium fluorides, or else alkali metal fluorides or mixtures of the compounds mentioned.

Examples of ammonium fluorides or phosphonium fluorides are those of the formula (VI)

(cation$^+$)(F$^-$)      (VI)

in which (cation$^+$) is a substituted quaternary ammonium or phosphonium cation, in particular a cation of the formula (VII)

[pnic($C_1$–$C_{12}$-alkyl)$_q$($C_6$–$C_{15}$-arylkyl)$_r$($C_5$–$C_{14}$-aryl)$_s$
({($C_2$–$C_6$-alkyl)-O]$_v$—($C_1$–$C_8$-alkyl)}$_t$)]$^{30}$      (VII)

in which pnic is nitrogen or phosphorus and in which, in each case, (q+r+s+t)=4.

In step A), preference is given to using alkali metal fluorides, in particular sodium fluoride, potassium fluoride and caesium fluoride, or mixtures thereof. Particular preference is given to potassium fluoride.

The molar ratio of ionic fluoride to bromine or chlorine atoms to be exchanged in compounds of the formula (III) may be, for example, 0.7 to 5, preferably 0.9 to 2 and more preferably 1.2 to 1.5. There is in principle no upper limit to the amount of ionic fluoride, but larger amounts are uneconomic.

Preference is also given to carrying out step A) in the presence of phase transfer catalysts and/or halex catalysts.

Suitable phase transfer catalysts are, for example, crown ethers such as 18-crown-6, 12-crown-4, dibenzo-18-crown-6 or dibenzo-12-crown4, cryptands such as cryptand [2.2.2] or podands such as polyglycol ethers or those of the formula (VIII)

(cation$^+$)(anion$^-$)      (VIII)

in which (cation$^+$) is as defined under the formula (VI) including its areas of preference and (anion⁻) is the anion of an organic or inorganic acid; preference is given to chloride, bromide, iodide, acetate, nitrate, sulphate, hydrogensulphate, tetrafluoroborate, hexafluorophosphate, tosylate, and triflate, and particular preference to chloride, bromide, iodide, sulphate and hydrogensulphate.

Halex catalysts are, for example, tetrakis(dialkylamino)phosphonium compounds (WO 98/05610) or those which are described in EP-A 1 266 904.

Preference is given to carrying out step A) also in the presence of organic solvent. Suitable organic solvents are, for example: ketones such as acetone, 2-butanone or methyl isobutyl ketone; nitriles, for example acetonitrile, propane nitrile, benzonitrile, benzyl nitrile or butyronitrile; amides, for example N,N-dimethylformamide, N,N-dimethylimidazolinone, N,N-dimethylacetamide, N-methylformanilide, N-methylpyrrolidone, N-methylcaprolactam or hexamethylphosphoramide; sulphoxides, for example dimethyl sulphoxide, sulphones, for example tetramethylenesulphone, polyethers, for example 1,4-dioxane, ethylene glycol dimethyl ether, ethylene glycol diethyl ether, diethylene glycol dimethyl ether or diethylene glycol diethyl ether, or mixtures of such organic solvents. Preferred solvents are: N,N-dimethylformamide, N,N-dimethylimidazolinone, N-methylpyrrolidone, dimethyl sulphoxide and tetramethylenesulphone.

The water content of the solvent is preferably not more than 1% by weight, preferably not more than 0.2% by weight and more preferably 0.05% by weight. Preference is given to achieving such a water content by incipient distillation or drying in a manner known per se. When alkali metal fluorides are used, particular preference is given to simultaneously drying or incipiently distilling the solvent in the presence of the alkali metal fluoride used.

The reaction temperature in step A) may be, for example, 120° C. to 250° C., preferably 160 to 220° C.

The reaction pressure may be, for example, 0.5 to 100 bar; preference is given to ambient pressure.

The reaction time may be, for example, 10 min to 72 hours, preferably 2 to 20 hours.

Step B) may be effected in analogy to processes which are known in principle, for example by hydrogenolysis of the compounds of the formula (IV) with a hydrogen donor in the presence of transition metal catalysts. Hydrogen donors are, for example, hydrazine, formic acid or formates, and also elemental hydrogen itself. Alternatively, the reduction may also be effected with zinc and ammonium formate in accordance with Tetrahedron Letters, 2002, 43,7, 1329–1331.

The process according to the invention for preparing fluorinated anilines features very simple and inexpensive preparation of the starting materials, for example by chlorination of anilines and subsequent oxidation to the azobenzenes, which progresses to synthesis of desired products in high yields. It is to be regarded as surprising that the halex reaction takes place at all and without formation of significant by-products under the conditions specified.

The compounds of the formula (I) which can be prepared in accordance with the invention are suitable in particular in a process for preparing pharmaceuticals and agrochemicals, as specified, for example, in WO-A 98/46607 and WO 98/46608.

This and other aspects of the invention are further described by the following illustrative but non-limiting examples.

EXAMPLES

Example 1

Preparation of 2,2',4,4',6,6'-hexafluoroazobenzene

With the exclusion of moisture, 4.3 g of dried potassium fluoride and 3.0 g of 2,2',4,4'6,6'-hexachloroazobenzene are initially charged in 51 g of sulpholane and 0.2 g of tetraphenylphosphonium bromide is added. Subsequently, the mixture is heated to 180° C. and stirred for 12 hours. After cooling, the mixture is discharged into 150 ml of water and extracted twice with 50 ml each time of cyclohexane. After crystallization, 1.7 g=76% of theory of the desired product is obtained.

Example 2

Preparation of 2,4,6-trifluoroaniline 1.0 g of 2,2',4,4',6,6'-hexafluoroazobenzene from Example 1 is dissolved at room temperature in 20 ml of methanol, and 0.6 g of ammonium formate and 0.5 g of zinc powder are added in succession. The mixture is stirred at room temperature for one hour. According to GC analysis, the starting material is then fully converted. After the methanol has been distilled off, the 2,4,6-trifluoroaniline is taken up in cyclohexane and is dried, and the solvent is distilled off again. 0.9 g of the desired product (89% of theory) remains.

Example 3

Preparation of 2,2'-bistrifluoromethyl-4,4'-difluoroazobenzene

In a similar manner to Example 1, 9.8 g of 2,2'-bistrifluoromethyl-4,4'-dichloroazobenzene, 4 g of potassium fluoride and 0.5 g of tetraphenylphosphonium bromide are reacted in 50 ml of sulpholane at 175° C. for 15 hours. After crystallization, 5.8 g of 2,2'-bistrifluoromethyl-4,4'-difluoroazobenzene (65% of theory) are obtained.

Example 4

Preparation of 2-trifluoromethyl-4-fluoroaniline 5 g of the product from Example 3 are dissolved in 60 ml of toluene and admixed with 0.2 g of 5% palladium on carbon. Subsequently, hydrogenation is effected at 60° C. and 20 bar of hydrogen for 5 hours. The conversion to the desired product is quantitative.

What is claimed is:

1. A process for preparing a compound(s) of the formula (I)

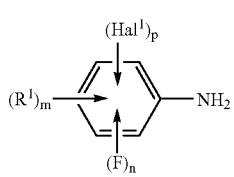

in which
m is an integer in the range from 0 to (5-n-p)
n is 1, 2, 3 or 4 and
p is 0, 1 or 2, where the sum of
n+p is a maximum of 4 and
$R^1$ is in each case independently hydrogen, fluorine, $C_1$–$C_{12}$-alkyl, $C_5$–$C_{14}$-aryl, $C_6$–$C_{15}$-arylalkyl, $C_1$–$C_{12}$-fluoroalkyl, $C_1$–$C_{12}$-fluoroalkylthio, $C_1$–$C_{12}$-fluoroalkoxy, $C_1$–$C_{12}$-alkylsulphonyl or radicals of the formulae (IIa) to (IIf)

A-CN (IIa)

A-CON($R^2$)$_2$— (IIb)

A-CO$_2R^2$ (IIc)

A-CONH$_2$ (IId)

A-COHal$^2$ (IIe)

A-B—$R^2$ (IIf)

where, in the formulae (IIa) to (IIf),
A is absent or is a $C_1$–$C_8$-alkylene or $C_1$–$C_8$-fluoroalkylene radical and
B is oxygen or $NR^2$, and
$R^2$ is in each case independently $C_1$-$C_8$-alkyl, $C_6$–$C_{15}$-arylalkyl or $C_5$–$C_{14}$-aryl, or $C_5$–$C_{14}$-aryl, or $N(R^2)_2$ as a whole is optionally a cyclic amino radical having a total of 4 to 12 carbon atoms and
$Hal^1$ is chlorine or bromine,
comprising:
in a step A), converting
a compound(s) of the formula (III)

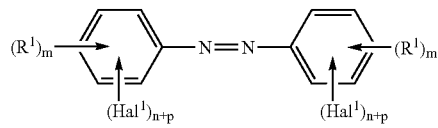

in which
$R^1$, $Hal^1$, m, p and n are each as defined above
in the presence of ionic fluoride to a compound(s) of the formula (IV)

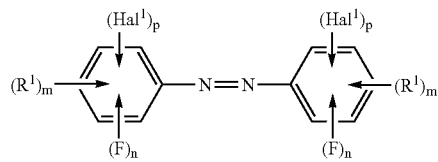

and,
in a step B), converting
the compound(s) of the formula (IV) to the compound(s) of the formula (I) with a reducing agent.

2. The process according to claim 1, wherein the compound(s) of the formula (I) are chosen from 2,4,6-trifluoroaniline, 2-trifluoromethyl-4-fluoroaniline, 4-trifluoromethyl-2-fluoroaniline, 4-trifluoromethyl-2,6-difluoroaniline and 3-trifluoromethyl-2,4,6-trifluoroaniline.

3. The process according to claim 1, wherein the compound(s) of the formula (III) is prepared, in a first step, by halogenating a compound(s) of the formula (V) to give a compound(s) of the formula (VI), where, in the formulae (V) and (VI)

$R^1$, $Hal^1$, n, p and m are each as defined in claim 1 and, in a subsequent step, oxiziding the—compound(s) of the formula (VI) to the compound(s) of the formula (III).

4. The process according to claim 1, wherein the ionic fluoride used is a quaternary ammonium fluoride, phosphonium fluoride, an alkali metal fluoride or a mixture thereof.

5. The process according to claim 1, wherein step A) is carried out in the presence of a phase transfer catalyst(s) and/or a halex catalyst(s).

6. The process according to claim 1, wherein step A) is carried out in the presence of an organic solvent(s).

7. The process according to claim 1, wherein the reaction temperature in step A) is 120° C. to 250° C.

8. 2,2'-Dichloro4,4'-bistrifluoromethylazobenzene, 2,2',6,6'-tetrachloro-4,4'-bistrifluoro-methylazobenzene, 2,2',4,4',6,6'-hexachloro-3,3'-bistrifluoromethylazobenzene and 4,4'-dichloro-2,2'-bistrifluoromethylazobenzene.

9. 2,2'-Difluoro-4,4'-bistrifluoromethylazobenzene, 2,2',6,6'-tetrafluoro-4,4'-bistrifluoro-methylazobenzene, 2,2',4,4',6,6'-hexafluoro-3,3'-bistrifluoromethylazobenzene and 4,4'-difluoro-2,2'-bistrifluoromethylazobenzene.

* * * * *